United States Patent [19]

Kopf-Sill et al.

[11] Patent Number: 5,590,052
[45] Date of Patent: Dec. 31, 1996

[54] ERROR CHECKING IN BLOOD ANALYZER

[75] Inventors: Anne R. Kopf-Sill, Portola Valley; Steven N. Buhl, Cupertino; Glenda L. Choate, Belmont; Lloyd A. Schick; Robert E. Nagle, both of Mountain View; Jenq C. Chang, San Jose; Daniel Bernstein, San Mateo; Wayne A. Britt, Sunnyvale, all of Calif.

[73] Assignee: Abaxis, Inc., Sunnyvale, Calif.

[21] Appl. No.: 227,554

[22] Filed: Apr. 14, 1994

[51] Int. Cl.$^6$ .................................................. G01N 21/17
[52] U.S. Cl. ...................... 364/498; 364/499; 356/427; 356/39; 436/43; 436/47; 436/48; 436/166
[58] Field of Search ...................... 356/427, 39; 436/43, 436/47, 48, 164–166; 364/496–499; 422/64

[56]  References Cited

U.S. PATENT DOCUMENTS

| | | | |
|---|---|---|---|
| 4,276,258 | 6/1981 | Ginsberg et al. | 364/497 X |
| 4,483,927 | 11/1984 | Takekaka | 364/497 X |
| 5,051,901 | 9/1991 | Endo | 364/497 X |
| 5,067,093 | 11/1991 | Przybylowicz et al. | 364/496 X |
| 5,112,134 | 5/1992 | Chow et al. | 356/427 OR |
| 5,304,350 | 4/1994 | Meserol | 436/446 X |

*Primary Examiner*—Emanuel T. Voeltz
*Assistant Examiner*—K. Shah
*Attorney, Agent, or Firm*—Townsend and Townsend and Crew LLP

[57] ABSTRACT

The present invention provides various methods for detecting errors in a blood analysis system. The system includes a blood analyzer and a molded plastic rotor with a series of chambers and capillary channels through which blood is processed and distributed to cuvettes which contain lyophilized reagents. The rotor is placed in the analyzer which spins the rotor, and an optical system reads the cuvettes as light is flashed through the cuvettes. The invention provides checks for: confirming the presence of a reagent in the cuvettes before a sample is applied to the cuvettes; determining whether a fluid sample has been properly distributed to the cuvettes of the rotor; determining whether an adequate amount of fluid sample was applied to the analytical rotor; determining whether a fluid sample has been properly distributed to a cuvette of an analytical rotor; determining whether a reaction chemistry in a cuvette has reached an end point; checking the noise level and non-linearity of a reaction rate in a cuvette; determining whether an adequate amount of diluent was delivered to the cuvettes of an analytical rotor; determining dilution systematic failure when measuring different reaction chemistries in the cuvettes of the rotor; determining whether a blood sample in a cuvette is hemolyzed, lipemic, or icteric; determining the degradation of a reagent in a cuvette; determining proper light source and light detector operation; and determining proper motor function and cuvette mark detection.

36 Claims, 16 Drawing Sheets

Place a fluid sample in the rotor and spin the rotor to deliver the sample to the plasma metering chamber and the overflow cuvette.

Flash the overflow cuvette with a 340nm flash.

Measure signal for the overflow cuvette (OVERFLOWcuv)

If OVERFLOWcuv < Insufficient Sample Limit, then indicate an error that an insufficient sample has been applied to the rotor.

FIG. 3

```
Place a fluid sample in the rotor and spin
the rotor to deliver the sample to the cuvettes.
```

```
Flash the first cuvette to receive the sample
with a 340nm flash.
```

```
Measure signal for the first cuvette (FIRSTcuv).
```

```
If FIRSTcuv < Sample to Cuvette Limit, then indicate an error that the sample has not
reached the cuvettes.
```

FIG. 4

```
┌─────────────────────────────────────────────────────┐
│ Determine two cuvettes (a,b) to be used as test     │
│ cuvettes.                                           │
└─────────────────────────────────────────────────────┘
                          │
┌─────────────────────────────────────────────────────┐
│ Flash the test cuvettes with a flash of 340nm.      │
└─────────────────────────────────────────────────────┘
                          │
┌─────────────────────────────────────────────────────┐
│ Measure a signal for the test cuvettes (cuv a,b)    │
└─────────────────────────────────────────────────────┘
                          │
┌─────────────────────────────────────────────────────┐
│ If cuv a/cuv b < Sample Diluent Mix Limit 1 OR      │
│ If cuv a/cuv b > Sample Diluent Mix Limit 2,        │
│                                                     │
│ then indicate an error that the diluent and sample  │
│ were not adequately mixed.                          │
└─────────────────────────────────────────────────────┘
```

FIG. 5

```
┌─────────────────────────────────────────────┐
│ Spin the rotor to deliver the diluent to the│
│ cuvettes.                                    │
└─────────────────────────────────────────────┘
                      │
┌─────────────────────────────────────────────┐
│ Flash the last cuvette to receive the diluent with │
│ a 850nm flash.                               │
└─────────────────────────────────────────────┘
                      │
┌─────────────────────────────────────────────┐
│ Measure a signal for the last cuvette (850cuv). │
└─────────────────────────────────────────────┘
                      │
┌─────────────────────────────────────────────┐
│ Flash the through hole with a 850nm flash.  │
└─────────────────────────────────────────────┘
                      │
┌─────────────────────────────────────────────┐
│ Measure the signal for the through hole (850opt). │
└─────────────────────────────────────────────┘
                      │
┌─────────────────────────────────────────────┐
│ If 850cuv/850opt < Insufficient Diluent Limit, │
│                                              │
│ then indicator an error that an insufficient amount │
│ of diluent has been delivered to the cuvettes. │
└─────────────────────────────────────────────┘
```

FIG. 9

```
┌─────────────────────────────────────────────┐
│      SPIN ROTOR AT STEADY SPEED (RPM)       │
└─────────────────────────────────────────────┘
                      │
┌─────────────────────────────────────────────┐
│      LOCATE INDEX MARK AND CALIBRATE        │
│            MARK WIDTH DETECTION             │
└─────────────────────────────────────────────┘
                      │
┌─────────────────────────────────────────────┐
│   DETECT WIDTH OF ALL CUVETTE MARKS AND     │
│   INDICATE ERROR CONDITION IF ANY WIDTH     │
│     FALLS OUTSIDE OF ACCEPTABLE RANGE       │
└─────────────────────────────────────────────┘
                      │
┌─────────────────────────────────────────────┐
│      DETECT DISTANCE BETWEEN MARKS AND      │
│    INDICATE ERROR IF ANY FALLS OUTSIDE OF   │
│            OF ACCEPTABLE RANGE              │
└─────────────────────────────────────────────┘
                      │
┌─────────────────────────────────────────────┐
│  COUNT CUVETTE MARKS IN FULL ROTATION BETWEEN│
│   APPEARANCE OF INDEX MARK AND INDICATE ERROR│
│           CONDITION IF NOT CORRECT          │
└─────────────────────────────────────────────┘
                      │
┌─────────────────────────────────────────────┐
│    CALCULATE MOTOR SPEED BASED ON RATE OF   │
│     PASSAGE OF CUVETTE MARKS, COMPARE WITH  │
│    SET SPEED, INDICATE ERROR IF DIFFERS BY  │
│             MORE THAN TOLERANCE             │
└─────────────────────────────────────────────┘
```

FIG. 15

ERROR CHECKING IN BLOOD ANALYZER

BACKGROUND OF THE INVENTION

1. Field of the Invention

This invention relates generally to the determination of fluid chemistries by photometric analysis. In particular, this invention provides methods for determining errors that can arise when using a photometric analyzer to analyze fluid chemistries which result in differential light absorption at different wavelengths.

2. Description of Background Art

Methods for using analyzers to photometrically determine fluid chemistries are known in the art. Before performing the analysis, a fluid sample is provided from a patient, which is typically blood or another body fluid, e.g., urine or saliva. In the case of blood, the sample is placed in a centrifugal rotor which is in turn placed in the analyzer where diluent is mixed with the blood sample. The analyzer rotates the rotor to separate the blood plasma from the blood's cellular components. After centrifugation, quantities of the separated fluid are mixed with diluent. Once the sample and diluent have mixed, the mixture is placed into sample cuvettes mixed with one or more reagents. Light of predetermined wavelengths is then passed through the cuvettes. Some of the light is partially absorbed by the products of the reactions between the reagents and the components of the fluid. The degree to which the light is absorbed at the wavelengths depends upon the concentration of the reaction product in the fluid sample.

By comparing the intensity of the light transmitted through the cuvette with a reference intensity, the concentration of a given product of the reaction between the fluid and the reagent can be determined. The concentration of the reaction is then used to calculate the concentration of a corresponding component in the sample fluid.

When using a photometric analyzer and a centrifugal rotor to determine fluid chemistries as described hereinabove, various errors can arise. For example, too little of the patient's fluid sample can be applied to the rotor. In such a case, the analyzer can produce an incorrect result if the reagents are not mixed with a sufficient sample volume. Similar errors can arise even if an adequate sample is delivered to each cuvette, if the reagent beads in the cuvettes do not dissolve as expected, or if the proper amount of diluent is not mixed with the sample. Errors can also occur if the wrong reagent is placed in a cuvette. Other errors can occur if the fluid sample has not been properly mixed with the diluent, or if the diluent used in the cuvettes is contaminated. Further potential errors can occur if the measurements are affected by system noise or if a chemistry is prematurely evaluated before reaching an end point. Incorrect readings can result if the blood sample is either hemolyzed, lipemic, or icteric, or if the reagents in the rotor itself are spoiled or degraded due to exposure to excessive heat, moisture, light, or other environmental factors.

Thus, it would be desirable to provide methods for detecting these and other problems in order to avoid the reporting of false results and improve the accuracy of the fluid analyzation process. The methods should be able to verify that individual readings and/or groups of readings fall within expected value(s) and range(s) and thus be able to produce an alarm when the readings are improbable and fall outside of the expected value(s) and range(s). The methods should further provide for specific checks to assure that critical functions of the rotor have been successfully completed such as dilution, cuvette filling, reagent dissolution, and the like. It would be further desirable that the methods, when applied to an analyzer, would be usable by individuals with little or no experience in using photometric analyzers.

SUMMARY OF THE INVENTION

The present invention provides methods for determining errors which may occur during the analysis of a fluid sample in a fluid analyzer. The methods are useful with a fluid analyzer which employs an analytical rotor having a plurality of cuvettes at its periphery. Some or all of the analysis cuvettes will contain a dried reagent, usually in the form of a bead. When a fluid sample is applied to the rotor, the sample is processed (usually including dilution with diluent) and aliquots of the sample are distributed to the cuvettes through a series of chambers and capillary channels. Within the cuvette, the sample dissolves the reagent and a reaction occurs which results in a color change depending on the amount of a particular analyte in the sample. Light is then directed through the cuvettes and light absorbance measurements are taken to determine the presence and/or amount of the analyte. To ensure that accurate readings are obtained, the present invention employs various methods for confirming proper operation of the fluid analyte system as follows. These methods are generally performed as part of the normal protocol of the analyzer and do not require significant participation by the user. For example, some checks are performed after a normal spinning of the rotor where the fluid sample is distributed to the cuvettes. This allows even an inexperienced user to operate the analyzer and still obtain accurate results.

In a first aspect, the present invention provides a method for confirming the presence of dried reagent in cuvettes of an analytical rotor before a fluid sample is applied to the cuvettes. The rotor includes a through hole in place of one of the cuvettes, and the through hole is used as a reference cuvette. Light is sequentially directed through each cuvette and an absorbance measurement is taken. Light is also directed through the through hole and a measurement taken. The measured absorbance signals for each cuvette are compared with the measured signal for the through hole to produce a comparison value for each cuvette. An error condition is indicated if the comparison value for any cuvette that should contain a dried reagent differs by at least a predetermined amount from a first value expected when a reagent is present. An error condition is also indicated if the comparison value for any cuvette that should not contain a dried reagent differs by at least a predetermined amount from a second value expected when a bead is absent. In a preferred aspect, the comparison value for each cuvette is obtained by dividing the measured signal for each cuvette by the measured signal for the through hole. This value is then compared against the expected values as described.

In a second aspect, the invention provides a method for determining whether a fluid sample (preferably blood and usually combined with diluent) has been properly distributed to cuvettes of an analytical rotor and whether the dried reagents dissolved as expected. This method is performed as part of the normal analytical protocol where the fluid sample is placed in the rotor and the rotor is spun to distribute aliquots of the sample to selected cuvettes. Usually, but not necessarily, the sample will be combined with diluent prior to distribution of the diluted sample. Light is then directed through each cuvette and through the through hole and corresponding signals are measured. The signals measured for each cuvette are then compared with the measured signal for the through hole to produce a comparison value for each cuvette. An error condition is indicated when the comparison value for any cuvette differs by at least a predetermined amount from a value expected when a proper distribution of the fluid sample is present. Preferably, the comparison value for each cuvette is obtained by dividing the measured signals for each cuvette by the measured signal for the through hole. If this value is less than the expected value, then an error condition is indicated.

The invention further provides a method for determining whether a sufficient amount of a fluid sample has been initially applied to an analytical rotor. This is accomplished by evaluating an overflow cuvette in the rotor which receives excess sample over that which is needed to distribute to each sample cuvette. As part of the normal analytical protocol, fluid is placed in the rotor and the rotor is spun to deliver the sample to a plasma metering chamber with the excess going to the overflow cuvette. Light is then directed to the overflow cuvette at a wavelength which is selectively absorbed by the fluid sample. A signal is measured from the light detector while light is directed through the overflow cuvette and is compared with a value expected when a threshold amount of sample is present. If the intended amount of sample was not applied to the rotor, insufficient overflow will be present and an error condition will be indicated. Preferably, the light directed to the overflow cuvette is at a wavelength in the range between 330 nm and 350 nm, and more preferably at 340 nm.

A further method is provided for determining whether a fluid sample has been properly distributed to a cuvette of an analytical rotor after placement of a diluted sample mixture in the cuvette. The method is performed by directing light through the cuvette at a wavelength which is selectively absorbed by the fluid sample but not by the diluent. Preferably, this is at a wavelength in the range of 330 nm to 350 nm, and more preferably at 340 nm. A signal is then measured from the cuvette while light is directed through the cuvette and compared with a value expected when sample is present. An error is indicated when the signal measured from the cuvette differs by at least a predetermined amount from the expected value. In one aspect of this method, the cuvette is a first cuvette in a sequence of cuvettes that is intended to receive the fluid sample. By checking the first cuvette, it can be determined that the fluid sample reached at least the first cuvette.

A method for determining whether a fluid sample has been properly mixed with diluent prior to distribution to a plurality of cuvettes of an analytical rotor is provided. After the diluent and fluid sample have been mixed, the mixture is distributed to the cuvettes of the rotor by spinning the rotor. Light is then directed through a multiplicity of the cuvettes at a wavelength which is differentially absorbed by t e mixtures having different ratios of the fluid sample and the diluent. Preferably, the light will have a wavelength in the range of 330 nm to 350 nm, and more preferably at 340 nm. To determine if the fluid sample and the diluent have been properly mixed, the signals measured from at least two of the cuvettes are compared with each other and an error condition is indicated if the range of the compared signals exceeds an expected range. Preferably, the measured signals are compared by dividing the measured signal for each of the multiplicity of cuvettes with each other.

The invention further provides a method for determining if diluent in an analytical rotor has been contaminated by bacteria or other materials. The method is performed by distributing diluent from a diluent source to a cuvette without combination with sample. Light is directed to the cuvette containing the diluent at a wavelength which is differentially absorbed by diluent having differing amounts of contamination and a resulting signal is measured. The signal measured is then compared with an expected value and an error is indicated if the measured signal differs by a predetermined amount from the expected value. Preferably, the light directed through the cuvette is at a wavelength in the range of 330 nm to 350 nm, and more preferably at 340 nm.

The invention provides yet another method for determining whether a reaction chemistry in a cuvette of an analytical rotor has reached an end point. The method provides for placing a fluid sample in a rotor and spinning the rotor to deliver the sample to the cuvette to initiate the reaction chemistry. This is according to normal analytical protocol. Light is then directed through the cuvette and a corresponding signal is measured. The steps of directing light through the cuvette and measuring the corresponding signal are repeated over time to obtain a series of measurements. These measurements are then adjusted and averaged to obtain an adjusted average. The range of the measured signals is also determined and compared with the adjusted average to obtain a comparison value. If the comparison value differs by more than a predetermined amount from a first allowable value, a flag is indicated that the end point has not been reached.

In one aspect of this method, the proper comparison value is determined by first evaluating the value of the adjusted average. If the range divided by the adjusted average is greater than this comparison value, the flag is indicated.

The invention provides a method for checking the non-linearity or noise level of reaction rate of a cuvette in an analytical rotor. According to the method, a fluid sample is delivered to the cuvette to initiate a reaction chemistry. Preferably, the fluid sample is blood and is placed in a rotor and the rotor is spun to deliver the sample to the cuvette. Light is then directed through the cuvette and a signal is measured and stored. The steps of directing light through the cuvette and measuring a signal are repeated over time to obtain a series of values. A regression analysis is then performed on the values to determine a best fit slope representing the reaction rate over time. A statistical analysis is also performed to determine the standard error of the slope using the stored values. The standard error of the slope is compared with the slope to obtain a comparison value. If the comparison value differs by a predetermined amount from an expected value, an error condition is indicated.

In one aspect of this method, only a portion of the stored values are selected to perform the regression analysis. These values preferably have a linear relationship. In another aspect of this method, the absolute value of the slope is evaluated to determine the proper comparison value. If the standard error of the slope divided by the slope is greater than the comparison value, then the error condition is indicated.

In a further method of the invention, a check is performed to determine whether an intended amount of diluent was packaged in an analytical rotor. This check is performed by evaluating the last cuvette of a plurality of cuvettes that are sequentially filled with diluent that is intended to receive the diluent. If diluent has not reached this cuvette, then an error signal is indicated. According to the method, the rotor is spun to sequentially deliver diluent to the cuvettes. Light is then directed through the last cuvette intended to receive the diluent and the corresponding signal is measured. The measured signal is then compared with an expected value and an error condition is indicated if the measured signal differs by a predetermined amount from the expected value.

The invention further provides a method for determining systematic failure when measuring different reaction chemistries in cuvettes of an analytical rotor. Sometimes systematic failure can occur if the sample is diluted too much. In that event, the analytes can all read the same percentage low. The method checks for this systematic failure by directing light through each cuvette having the fluid sample. The signal is measured for each cuvette and compared with an associated expected value according to the particular reaction chemistry in the cuvette. If a certain percentage of the measured signals are below the associated expected value, an error condition is indicated that the result is very unusual and the sample should be run again. In one aspect of this method, an error signal is indicated if both the total protein and potassium assays are both below their associated expected values.

The invention provides a method for determining whether a fluid sample in a cuvette of an analytical rotor is hemolyzed, lipemic, or icteric. Preferably, the sample will be a blood sample which is applied to the rotor and the rotor is spun to separate plasma from the blood and to direct the plasma to the cuvette. The cuvette contains a dried sample blank reagent. Light having a first wavelength is directed through the cuvette containing diluted sample mixture and measured. The steps of directing light and measuring the corresponding signal are repeated twice more using a second and third wavelength of light. The three signals measured from the cuvette for each of the three wavelengths are compared in an iterative fashion using a series of equations to determine whether the sample is hemolyzed, lipemic, or icteric. If any of these conditions are met, an error condition is indicated. Preferably, the first wavelength is in the range of 330 nm to 350 nm, and more preferably is 340 nm, the second wavelength is in the range of 395 nm to 415 nm, and more preferably is 405 nm, and the third wavelength is in the range of 457 nm to 477 nm, and more preferably is 467 nm.

A further method of the present invention determines whether some of the chemistries in an analytical rotor have been affected by excessive exposure to heat, humidity, or light. The check is performed by providing at least one test reagent in at least one cuvette which is more sensitive to heat, light, or moisture than all other analytical reagents in other cuvettes. The test reagent is diluted with diluent and light having a selected wavelength is directed through the cuvette. A signal is measured from the light detector for the cuvette while light is directed through the cuvette and the signal measured is compared with an expected value. If the measured signal differs by at least a predetermined amount from the expected value, an error condition is indicated. In a preferred aspect of this method, the test reagent is selected from the group consisting of uric acid, d-lactate dehydrogenase, and urease, and the wavelength of light is between 340 nm and 550 nm.

Further methods of the present invention determine proper light source and/or light detector function by measuring detected light under full and blocked light conditions and analyzing the detected light to see if light output is acceptable and if the detector is affected by excessive noise from the light or other sources.

A further method of the present invention determines proper motor function and cuvette mark detection by detecting the passage of cuvette marks as the rotor is spun at a predetermined speed and determining whether the observed speed and mark characteristics fall within expected ranges.

BRIEF DESCRIPTION OF THE DRAWINGS

FIG. 3 is a flow chart illustrating a method for determining whether an intended amount of a fluid sample was applied to an analytical rotor.

FIG. 4 is a flow chart illustrating a method for determining whether a fluid sample has been properly distributed to a cuvette of an analytical rotor.

FIG. 5 is a flow chart illustrating a method for determining whether a fluid sample has been properly mixed with diluent prior to distribution to a plurality of cuvettes in an analytical rotor.

FIG. 9 is a flow chart illustrating a method for determining whether an intended amount of diluent was delivered to the cuvettes of an analytical rotor.

FIG. 15 is a flow chart illustrating a method for determining proper motor function and cuvette mark detection.

DETAILED DESCRIPTION OF THE SPECIFIC EMBODIMENTS

The present invention provides methods for checking errors that can arise when analyzing a fluid sample by subjecting the sample to known chemical reactions (i.e., reacting the sample with particular reagents under controlled conditions) which result in changes which are detectable in a photometric analyzer. The changes will usually be in light absorbance at one or more wavelengths, and analysis will be effected by passing a light beam through the sample, determining absorbance at the wavelength(s), and calculating concentrations of one or more analytes in the sample based on such a measured absorbency.

The methods of the invention are used with a fluid analyzer system which includes a receptacle holder having a plurality of sample receptacles. The fluid sample is subjected to known chemical reactions in the sample receptacles. Light is then directed through the sample in the sample receptacles where the absorbance is determined. The particular geometry of the receptacle holder is not critical as long as it contains the sample receptacles. For example, the receptacle holder can be a rotatable turntable (or carousel) or an analytical rotor with the sample receptacles at the outer periphery. Alternatively, the receptacle holder can be rack holder or microtiter plate with the sample receptacles arranged in rows or columns. The sample receptacles must be capable of holding the sample fluid and the reagent and should be substantially clear to allow for photometric analysis of the sample. For example, the sample receptacles can be cuvettes at the periphery of an analytical rotor, reaction tubes at the periphery of an automated carousel, or test tubes in a rack holder. Suitable receptacle holders for use with the methods of the present invention are described in U.S. Pat. Nos. 4,158,545; 4,220,607; 4,383,041; 4,536,369; 4,540,549; and 4,837,159, the disclosures of which are herein incorporated by reference. For purposes of the remaining discussion, the methods of the present invention will be described in the context of an analytical rotor of the type which is spun at a high rotational speed to separate plasma from blood and distribute aliquots of the separated plasma to a plurality of cuvettes at its periphery. The analytical rotor is analogous to the receptacle holder and the cuvettes are analogous to the sample receptacles. The invention, however, is in no way limited to only the use of an analytical rotor.

The present invention is particularly directed to photometric analyzers employing a centrifugal analytical rotor having a plurality of peripheral cuvettes, such as the analyzer and rotors described in U.S. patent application Ser. No. 08/040,549, U.S. Pat. Nos. 5,061,381; 5,173,193; 5,186,844; 5,122,284; and U.S. patent application Nos. 07/747,179; 07/783,041; 07/833,689; and 07/862,041, the complete disclosures of which are incorporated herein by reference.

Figure 16:
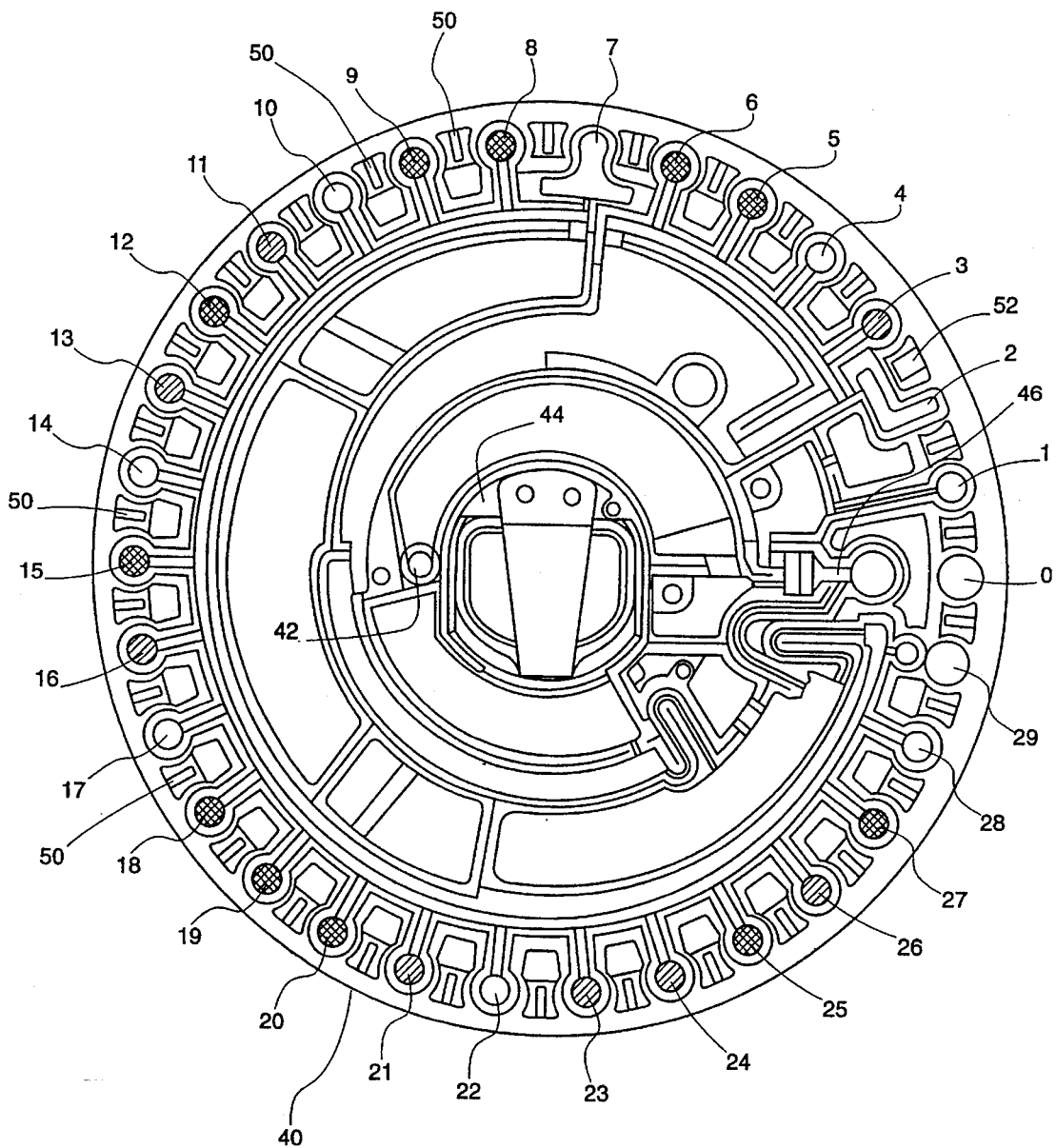
FIG. 16 illustrates an exemplary analytical rotor that can be used with the methods of the present invention.

A preferred rotor comprises a series of many interlinked internal chambers and passages. Fluid flow through the rotor is controlled by a series of stop junctions, capillaries, and siphons acting in conjunction with centrifugal force applied by spinning the rotor in the analyzer. An exemplary rotor 40 that can be used in accordance with the principles of the present invention is shown in FIG. 16. For purposes of convenience in describing the invention, reference to rotor 40 will be made. However, the invention is in no way limited to the use of rotor 40, but can be used with any analytical rotor used in a photometric analyzer.

A fluid sample, usually blood, is applied to the rotor 40 through a blood application port 42. The rotor 40 is then placed into the analyzer and is loaded onto a spindle. The spindle is coupled to a motor which is able to spin the rotor. Upon initiation of spinning, diluent contained in a diluent container 44 is released and allowed to mix with a predetermined amount of the blood sample. As the rotor 40 spins inside the analyzer, the blood sample mixes to homogeneity with the diluent. As the rotor continues to spin, the blood cells are separated from the diluted plasma primarily by centrifugal force. After separation and mixing, the diluted plasma is sequentially distributed through the internal chambers of the rotor 40 into test wells or cuvettes 1–28.

The cuvettes are preferably located at the outer periphery of the rotor 40. Some of the cuvettes are designated as assay cuvettes and contain reagents, e.g., cuvettes 3, 5, 6, 8, 9, 11–13, 15, 16, 18–21, and 23–27. The reagents can be any type of reagent capable of dissolving in the sample and producing a detectable signal. Preferably, the reagents used will be specially formulated dried reagent beads or spheres. One or more reagent spheres comprising the reagents necessary for a desired assay are provided in each of the assay cuvettes. The reagent beads dissolve as the plasma enters the cuvette, and chemical reactions are initiated between components of the diluted plasma and the reagent beads. Reagent beads suitable for use in the assay cuvettes are described in U.S. patent application Ser. No. 747,179, the complete disclosure of which is hereby incorporated herein by reference. Alternatively, the reagents can be painted in the cuvettes and will dissolve when contacting the plasma.

Other cuvettes around the rotor do not contain the reagent, and no chemical reactions take place in these cuvettes. Instead, these cuvettes serve other purposes. For example, cuvette 1 serves as an overflow cuvette. After sample is placed in the rotor 40, the rotor 40 is spun to deliver the sample to a plasma metering chamber 46 with the excess above that which is required to distribute to the cuvettes going to the overflow cuvette 1. Cuvette 1 can be then be evaluated to determine if sample was sequentially delivered to the cuvettes.

A through hole 29, i.e. a physical opening in the rotor 40, is placed at position 29 and is used as a "reference cuvette." Other cuvettes also serve as reference cuvettes. Measurements taken through the reference cuvettes are compared with measurements taken through the assay cuvettes as part of the test procedure. Instead of using a through hole as a reference cuvette, the analyzer can be "blanked on air," i e. the analyzer can direct light through an open aperture and onto the photodetector. The resulting measurement can be used as a reference.

The chemical reactions taking place in the assay cuvettes are monitored photometrically, i.e., light is directed or flashed through the assay cuvettes onto a photodetector within the analyzer to produce an output signal. The output signal is directly or inversely proportional to the amount of a reaction product which results from reaction between an analyte and one or more of the reagent components. Thus, concentrations can be determined using well-known methods and algorithms. When taking photometric measurements it is preferred to take a "flash set" of measurement, i.e. a set of measurements taken at close intervals of time. The measurements from the flash set are then averaged and used as the measurement value. Preferably, the flash set will use a series of ten measurements from ten flashes which will be averaged to produce the measured value. For convenience of discussion, whenever the taking of measurements by directing light through the cuvettes or the through hole is discussed hereinafter, it is assumed that it may include the taking a flash set.

Various tests can be performed automatically by the analyzer. Most of the tests are end point tests; i.e., the result is computed based on the amount of a given reaction product in a cuvette when the reaction is completed. Other tests are rate tests which depend on the rate of formation of a known reaction product within the cuvette. Each test is performed by the analyzer according to known and accepted analytical procedures and algorithms.

For any test performed by the analyzer, a sufficient fluid sample must be applied to the rotor so that the sample actually reaches the assay cuvettes after being spun by the rotor. It is also essential that the diluent is properly mixed with the fluid sample and that the diluent is not contaminated. It is further necessary that a correct amount of diluent is mixed with a+correct amount of fluid sample. Furthermore, it is necessary that the reagent has not become spoiled or degraded when performing the analysis. As described in detail hereinafter, the present invention provides a series of checks to identify the occurrence of such events.

In the event of that error is determined, the analyzer can be configured to send a specific signal to the user indicating the particular error. Alternatively, or in addition, the analyzer can suppress the rotor and prevent further measurements from taking place until the rotor is removed from the analyzer.

Figure 1:
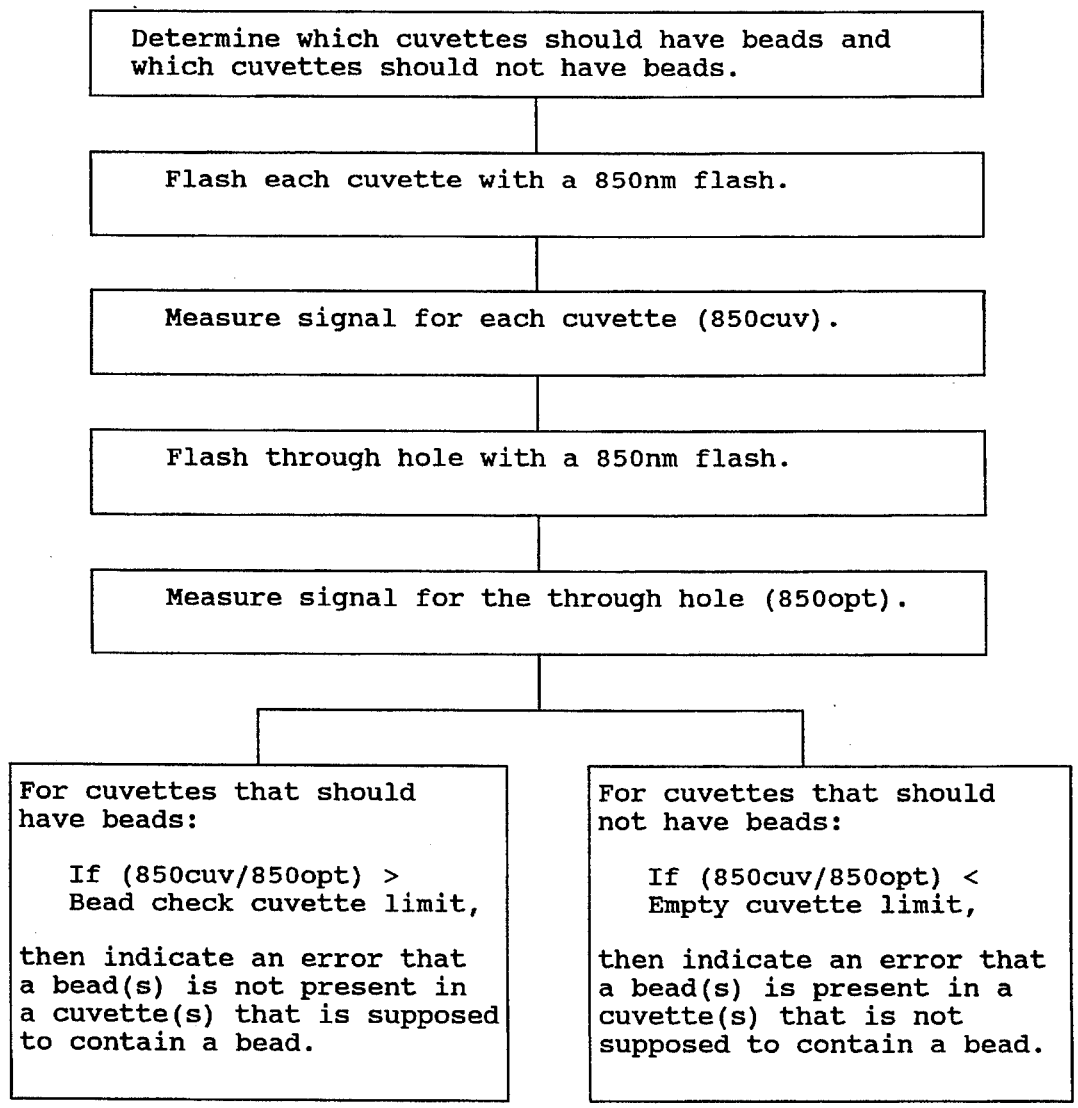
FIG. 1 is a flow chart illustrating a method for determining the presence of a reagent bead in cuvettes of an analytic rotor before a fluid sample is applied to the cuvettes.

Referring to FIG. 1, a method for determining the proper distribution of reagent in the cuvettes of the analytical rotor will be described. As previously described, the analytical rotor is designed so that only certain cuvettes are to contain a reagent(s). During the manufacture of the rotor, the reagent(s) can accidentally be placed in cuvettes that are not supposed to contain the reagent(s). Alternatively, cuvettes that are supposed to contain the reagent(s) may not. Hence, the method described in FIG. 1 is used to determine whether the reagent(s) were properly distributed to the cuvettes of the rotor.

Before the check is initiated, a desired distribution scheme for the reagent is determined. This information is typically stored in the analyzer's processor and depends on the specific rotor to be used. The rotor is then placed in the analyzer and light is sequentially directed through each cuvette before a fluid sample is applied to the rotor. The light flashed through each cuvette is measured and compared to the transmittance of light that is passed through the through hole of the rotor. Preferably, the wavelength of the light is in the range of about 840 nm to 860 nm, and more preferably at 850 nm for both the cuvettes and the through hole.

When a reagent is present in a cuvette, light transmission is dramatically reduced. Thus, for cuvettes that should contain reagent, the measured signal compared to the signal through the through hole should be relatively low. If the signal is high, then a reagent is not likely present and the analyzer will generate a signal indicating that a reagent is not present in a cuvette that is supposed to contain a reagent. Alternatively, the analyzer may simply suppress results of the rotor.

For cuvettes that should not have reagent, the signal measured through the cuvette should be relatively large when compared to the light through the through hole. If the value is small in comparison to the through hole value, it is likely that a reagent is present in the cuvette. The analyzer then signals an error that a reagent is present in a cuvette that is not supposed to contain a reagent.

This check can also be used to detect a rotor that has been severely handled, or in which the reagent beads have shattered. If the beads are shattered, light can pass through the cuvette during the check and cause the analyzer to generate an error signal.

As shown in FIG. 1, the method will preferably divide the measured signal for each cuvette with the signal measured through the through hole. This value is compared to one of two limits, depending on whether the cuvette should or should not contain a reagent. These values are empirically determined, based on the particular reagent used in the cuvette. For example, for cuvettes that should not have reagent, the ratio between the signal measured through the empty cuvette and the signal measured through the through hole should be greater than about 0.7 when 850 nm light is used. If the ratio is less than 0.7, than an error signal is indicated. For cuvettes that should have reagent, if the ratio is greater than about 0.2 when 850 nm light is used, an error is indicated.

Figure 2:
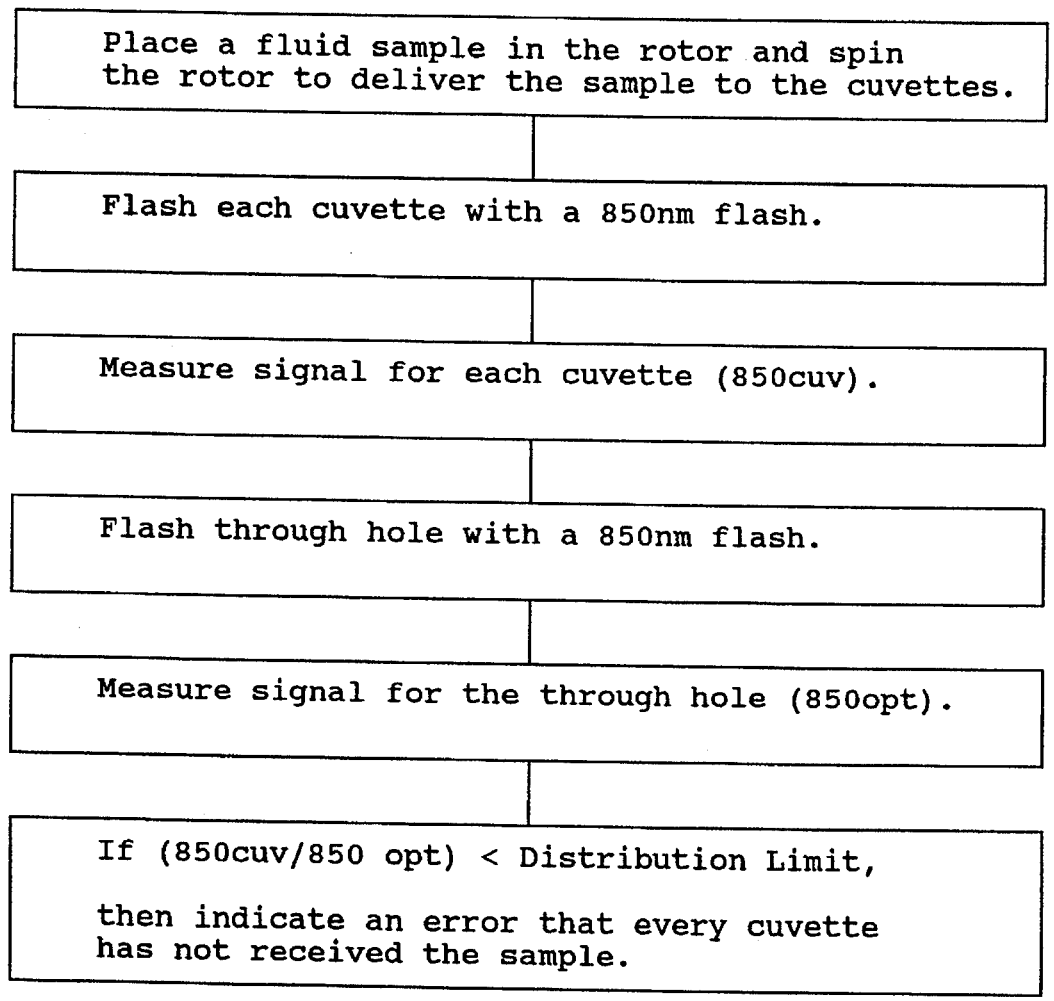
FIG. 2 is a flow chart illustrating a method for determining whether a fluid sample has been properly distributed to the cuvettes of an analytical rotor.

Shown in FIG. 2 is a method for determining whether a fluid sample applied to the rotor has reached every cuvette, and that the reagent in the cuvettes dissolve as expected. Before the check is performed, a fluid sample is placed in the rotor and the rotor is spun to deliver the sample to the cuvettes. Each of the cuvettes is then flashed with light and a signal is measured for the light passing through each cuvette. Preferably, each cuvette will be flashed with light having a wavelength of about 850 nm. The through hole is also flashed with light and a signal is measured. The signal measured through each cuvette is then compared with the signal measured through the through hole to obtain a comparison value for each cuvette. If the comparison value for each cuvette differs by a predetermined amount from an expected value when a proper distribution of the fluid sample is present in each cuvette, an error condition is indicated. This error reflects that every cuvette has not received sample.

In a preferable aspect of this method, the comparison value is compared to a distribution limit. If the comparison value is less than the distribution limit, the error is indicated. Preferably, the distribution limit is the same for all cuvettes, regardless of the type of reagent in the cuvettes and whether a reagent is supposed to be present. An exemplary distribution limit when 850 nm light is used is 0.3.

As previously described, the analytical rotor of FIG. 16 contains an overflow cuvette 1 which receives any excess fluid sample beyond that which is needed to distribute a sufficient volume sample to each cuvette. As shown in FIG. 3, overflow cuvette 1 is checked to see if sample is present. Since the overflow cuvette fills after the plasma metering chamber, if no sample is present in the overflow cuvette, an error is indicated that an insufficient sample has been applied to the rotor.

When using this method with the exemplary rotor 40 of FIG. 16, the fluid sample is applied to the fluid application port 42. The rotor 40 is then placed in the analyzer and spun to deliver the sample to the cuvettes 1–28. The overflow cuvette 1 is then flashed with about a 340 nm flash and a signal is measured. If the measured signal is less than an insufficient sample limit, then an error is indicated that an insufficient sample has been applied to the rotor. An exemplary insufficient sample limit is 0.03. The use of light at about 340 nm is preferred because all samples, including serum and plasma as well as whole blood, have a detectable absorbance at about 340 nm. If the sample is present in the overflow cuvette 1, the analyzer will be able to detect an absorbance. Hence, the analyzer can check to determine if the user put in too little sample or no sample at all.

As shown in FIG. 4, the invention provides a method for determining if a fluid sample applied to an analytical rotor has reached the cuvettes. This is accomplished by checking the first cuvette intended to receive a sample to make sure sample arrived at that cuvette. This is performed by flashing the first cuvette with about a 340 nm absorbance and measuring the resulting signal. Light having a wavelength of about 340 nm is preferred since the sample will absorb at about 340 nm, whereas straight diluent will not. The measured signal is then compared to a sample-to-cuvette limit to determine if the sample has reached the cuvette.

In the exemplary rotor of FIG. 16, the first cuvette to receive sample is cuvette 28. After a fluid sample is placed in the application port 42 and spun to deliver the sample to the cuvettes, light is flashed through cuvette 28 and a measurement is taken. If this measurement is less than the sample-to-cuvette limit, then an error is indicated that the sample has not reached the cuvette. An exemplary sample-to-cuvette limit is 0.04 when 340 nm wavelength light is used.

FIG. 5 illustrates a method for determining whether a fluid sample has been properly mixed with diluent prior to distribution to the cuvettes of an analytical rotor. After mixture, the check is performed by spinning the rotor to deliver the fluid sample and diluent mixture to the cuvettes. Light is then flashed through a selected number of the cuvettes with a wavelength of light which is differentially absorbed by mixtures having different ratios of the fluid sample and the diluent. Preferably, the wavelength of light is about 340 nm. The selected cuvettes through which the light is flashed are preferably cuvettes which do not have a reagent and which are spaced around the periphery of the rotor, such as cuvettes 17 and 28. The measured signals through the cuvettes are then compared with each other to determine if they are approximately equal. If the measurements significantly vary, then an error will be indicated that the diluent and sample were not adequately mixed.

As shown in FIG. 5, an exemplary way to compare the measured signals is to select two of the measurements and divide one by the other. The resulting value is then evaluated to determine if it falls within an acceptable range. If the acceptable range is exceeded, then the error condition is indicated. Additionally, another cuvette can be filled only with diluent, such as cuvette 4, and be used as a reference cuvette since 340 nm wavelength light is not absorbed by straight diluent. Light directed through this cuvette provides a reference value. Before the two measurements are divided, each has subtracted from it the reference value.

Figure 6:
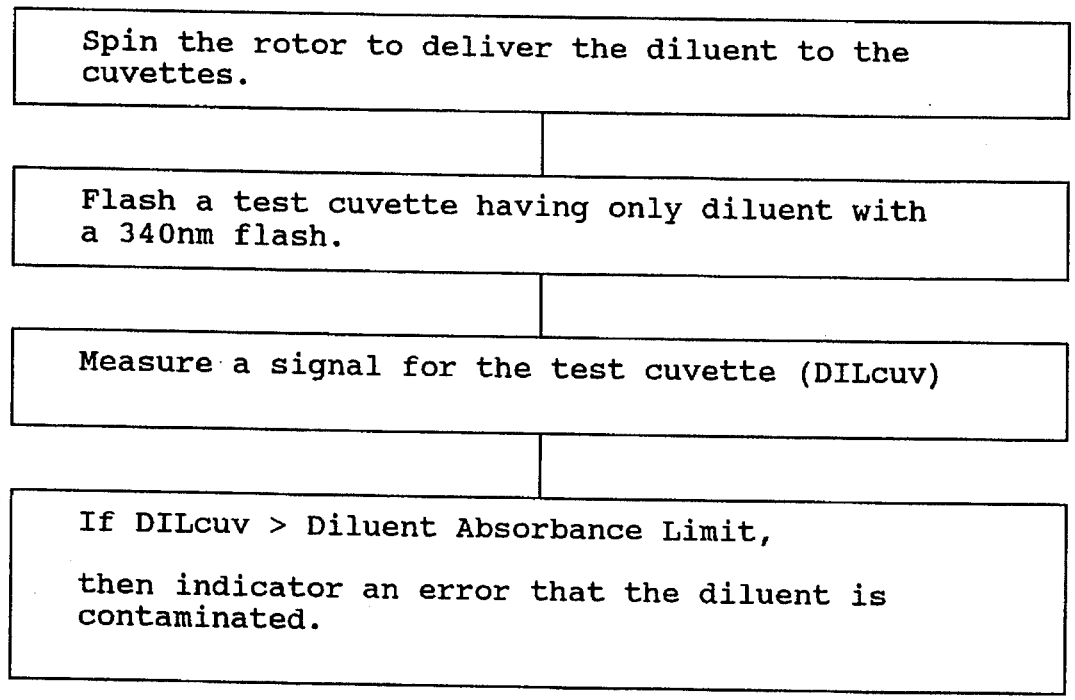
FIG. 6 is a flow chart illustrating a method for determining whether diluent distributed to cuvettes of an analytical rotor is contaminated.

Sometimes diluent in the rotor can become contaminated by bacteria or other materials. The method illustrated in FIG. 6 is used to determine whether diluent distributed to the cuvettes of the rotor is contaminated. After diluent has been distributed to the cuvettes, light is flashed through one of the cuvettes which contains only diluent, such as cuvette 4. Light directed through this cuvette has a wavelength which is differentially absorbed by diluent having differing amounts of contamination. A preferable wavelength of light is about 340 nm. The signal measured through this cuvette is compared with a diluent absorbance limit. If the measured value differs from this limit by a predetermined amount, an error is indicated that the diluent is contaminated and the rotor can be suppressed. In a preferred aspect, the measured signal is compared with the diluent absorbance limit to determine if the measured signal is greater than the limit. If so, the error signal is indicated.

Figure 7:
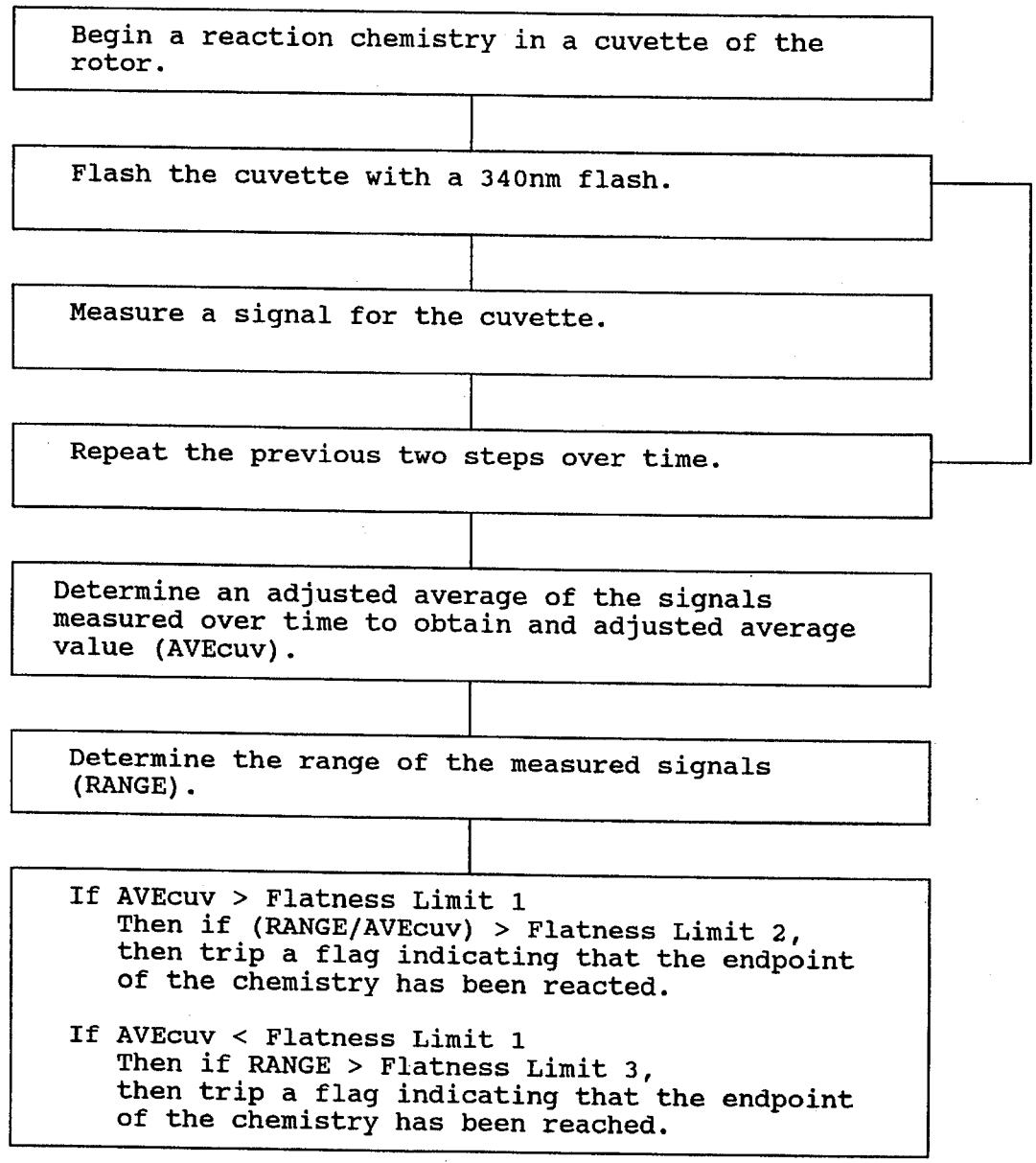
FIG. 7 is a flow chart illustrating a method for determining whether a reaction chemistry in a cuvette of an analytical rotor has reached an end point.

FIG. 7 illustrates a method for determining whether a reaction chemistry in a cuvette of an analytical rotor has reached an end point. This is accomplished by evaluating the absorbance levels through the cuvettes over time to determine if the levels remain approximately constant. If so, a conclusion can be reached that the chemistry has reached its end point. The check has begun by placing a fluid sample in the rotor and spinning the rotor to deliver the sample to the cuvette to initiate the reaction chemistry within the cuvette. Light is flashed through the cuvette and a signal is measured. The wavelength of light can vary depending on the particular chemistry. After a period of time, the cuvette is flashed with the same wavelength of light and the corresponding signal measured. These steps are repeated over time as necessary to obtain a plurality of measured signals through the cuvette over time. Preferably, these measurements will be taken about every 20 seconds.

The measurements are then scaled, and/or adjusted, and averaged to obtain an adjusted average of the signals measured over time. Further, the range of the measured signals is determined. The range is then compared with the adjusted average to obtain a comparison value. If the comparison value differs by a predetermined amount from a first allowable value, then a flag is indicated that the end point of the chemistry has not been reached. As shown in FIG. 7, this is preferably accomplished by dividing the range by the adjusted average to obtain the comparison value. If the comparison value is greater than a flatness limit, then the flag is tripped.

Depending on the particular chemistry, the comparison value can greatly vary. Therefore, the method in FIG. 7 evaluates the adjusted average before performing the comparison to determine the appropriate flatness limit. Hence, the method for determining whether a reaction chemistry has reached its end point can be adapted to a variety of different chemistries.

Figure 8:
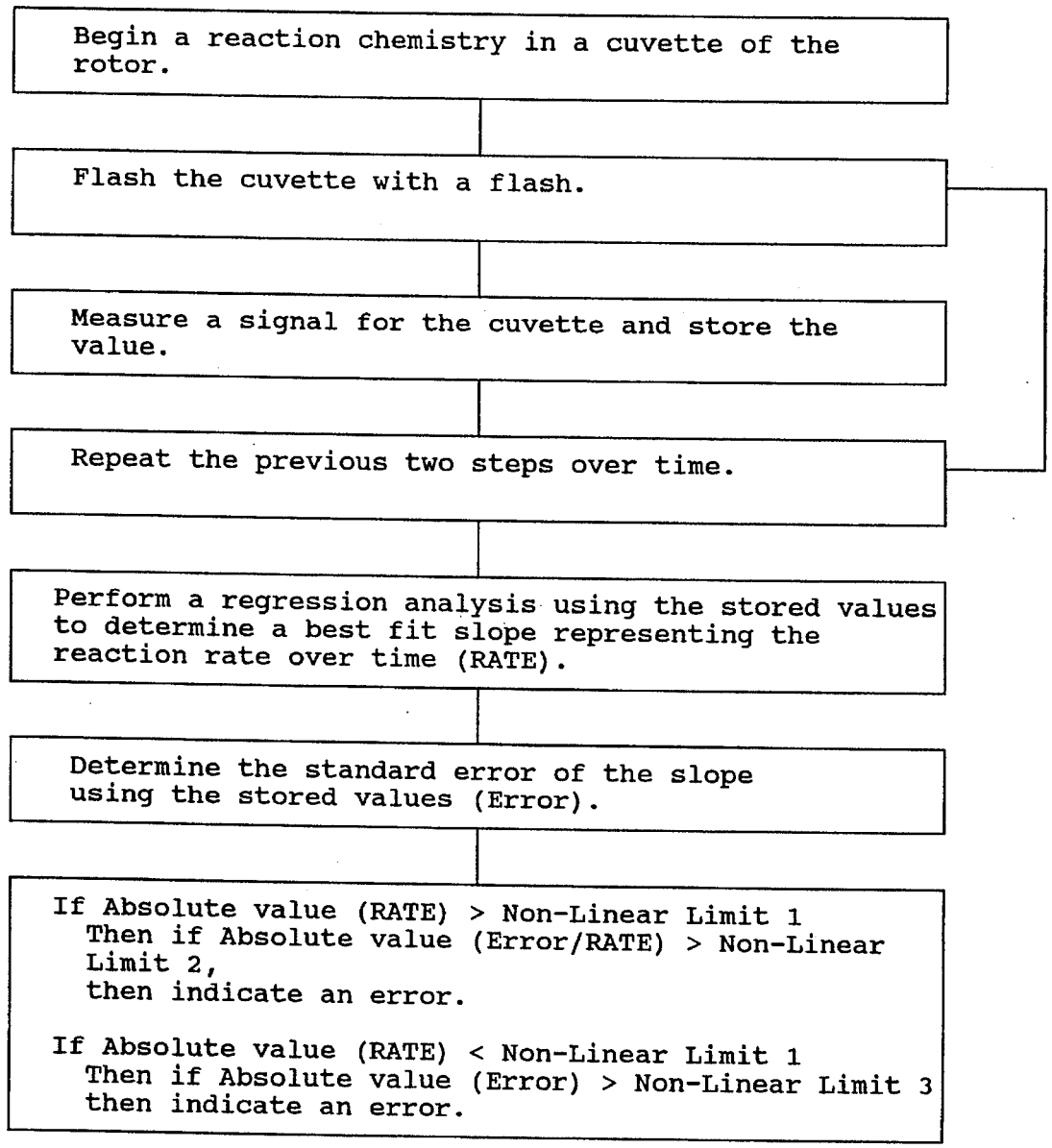
FIG. 8 is a flow chart illustrating a method for checking the linearity and noise level of a reaction rate in a cuvette of an analytical rotor.

FIG. 8 illustrates a method for checking the linearity and noise level of a reaction rate in the cuvette of an analytical rotor. The check is performed by placing a fluid sample in the rotor and spinning the rotor to deliver the sample to the cuvette to initiate a reaction chemistry. Light is then directed to the cuvette and a signal is measured and stored. The steps of flashing and measuring are then repeated over time in a manner similar to that discussed in connection with FIG. 7. A regression analysis is then performed using the stored values to obtain an equation representing the stored values over time. From the equation a best fit slope is obtained representing the reaction rate over time. A statistical analysis is also performed on the stored values to determine the standard error of the slope. The standard error of the slope is then compared with the slope to obtain a comparison value. If the comparison value differs by at least a predetermined amount from a first allowable value, an error condition is indicated.

Most chemistries in the cuvettes have reaction rates that are linear. Hence, if the absolute value of the error divided by the slope is greater than a non-linear limit, the error condition is indicated. The method of FIG. 8 can be used with the various different reaction chemistries in a manner similar to that discussed in connection with FIG. 7 by evaluating the value of the slope to determine the appropriate non-linear limit.

In a further aspect of this method, a step is included to insure the appropriate measured values are used. Preferably, the entire set of measured values is used. However, when the signals are measured over time, only a portion of the values may have a linear relationship. This can result if the substrate in the cuvettes has been depleted over time. Depletion of the substrate can occur depending on the particular sample which in turn depends on the state of the patient. For example, in some patients, the rate will be extremely steep and will rapidly deplete the substrate. Measurements taken after the substrate have been depleted will not be accurate and should not be included in the analysis. To account for this, a further step can be included to determine which values have a linear relationship. Only these values are then used in the analysis.

To determine which measured values have a linear relationship, the last measurement is compared to a substrate depletion level where all the substrate is depleted. If the last value is greater than the substrate depletion level, all the previously measured values are used in the analysis. If not, one of the measurements taken near a half-way point is compared to the substrate depletion level. If the half-way value is greater than the substrate depletion level, the previously measured values (up to the half-way value) are used in the analysis. If not, a third measured value is compared to the substrate depletion level. If the third value is less than the substrate depletion level, a substrate depletion error is indicated and the results of the chemistry are suppressed. If not, the first three values are used in the analysis.

FIG. 9 illustrates a method used to determine whether an intended amount of diluent was delivered to the cuvettes of to an analytical rotor. If the rotor has not been supplied with sufficient diluent, each cuvette may not receive a proper distribution of diluent which can adversely affect the chemistries. This check is performed by spinning the rotor to deliver the diluent to the cuvettes. The last cuvette that is intended to received the diluent is then flashed with a wavelength of light that is selectively absorbed according to the amount of diluent. In the exemplary rotor of FIG. 16, cuvette 3 is the last rotor intended to receive the diluent. Preferably, the wavelength of light used to flash the cuvette is about 850 nm. The through hole 29 is also flashed with about a 850 nm flash and a signal is measured. The signal measured through the cuvette is then compared with the signal measured through the cuvette to obtain a comparison value. If the comparison value differs by a predetermined amount from an expected value, an error signal is indicated that an insufficient amount of diluent has been delivered to the cuvettes.

Preferably, the signal measured through the cuvette and the signal measured through the through hole will be compared by dividing the signal measured to the cuvette by the signal measured through the through hole. If this value is less than an insufficient diluent limit, the error signal is indicated. An exemplary insufficient diluent limit when 850 nm wavelength light is used is 0.30.

Figure 10:
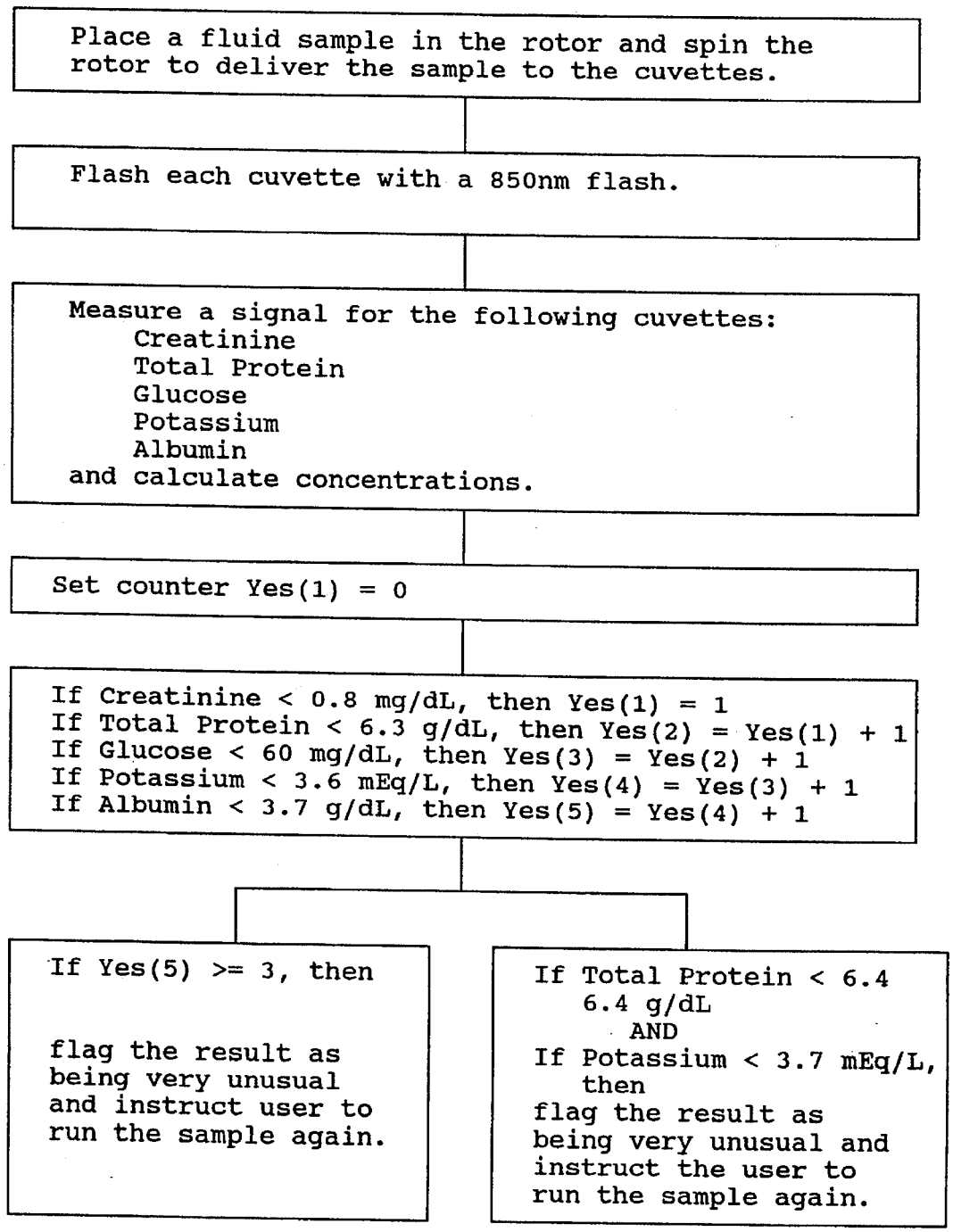
FIG. 10 is a flow chart illustrating a method for determining systematic failure when measuring different reaction chemistries in cuvettes with an analytical rotor.

On occasion, the measurements taken through the analytical rotor experience a "systematic error." For example, too little sample may reach the cuvettes, e.g., 20–80% too little. In such an event, all the analytes read the same percentage low, e.g., 20%. Since a number of different analytes are used, it is statistically unlikely that most or all of the analytes will be systematically low. FIG. 10 illustrates a method used to determine systematic error when measuring different reaction chemistries in cuvettes of an analytical rotor.

Initially, a fluid sample is placed in the rotor and the rotor is spun to deliver the sample to the cuvettes. Each cuvette is then flashed with light and a suitable wavelength monitored. The resulting signal is converted to concentration for each of the chemistries and is compared with an expected value according to the particular reaction chemistry occurring in the cuvette. The total number of cuvettes which differ by a predetermined amount from each associated expected value is then determined. If this total is greater than an acceptable value, an error condition is indicated that the result is very unusual and that the user should run the sample again.

As an example, some of the reaction chemistries in an analytical rotor can include creatinine, total protein, glucose, potassium, and albumin. If three or more of these chemistries are unexpectedly low, the error condition is be indicated. Further, if total protein and potassium are both below their expected values, then the error condition is indicated.

Although described in the context of an analytical rotor, the method described in connection with FIG. 10 can be applied to any system that measures the presence of two or more analytes in a sample and where dilution errors can arise. When measurements are taken, the results can be statistically unlikely. As an example, if the concentration of nine analytes were measured, it may be statistically unlikely that all nine measurements would be 50% low. Alternatively, it may be statistically unlikely if eight of the nine measurements would be 60% low, or that seven of the nine measurements would be 70% low. The method of the invention evaluates the number of measurements that are either too small or too large (as well as the extent of the variance) and determines whether this is a statistically unlikely result. If so, a flag is set warning the user that the results may not be accurate.

Figure 11:
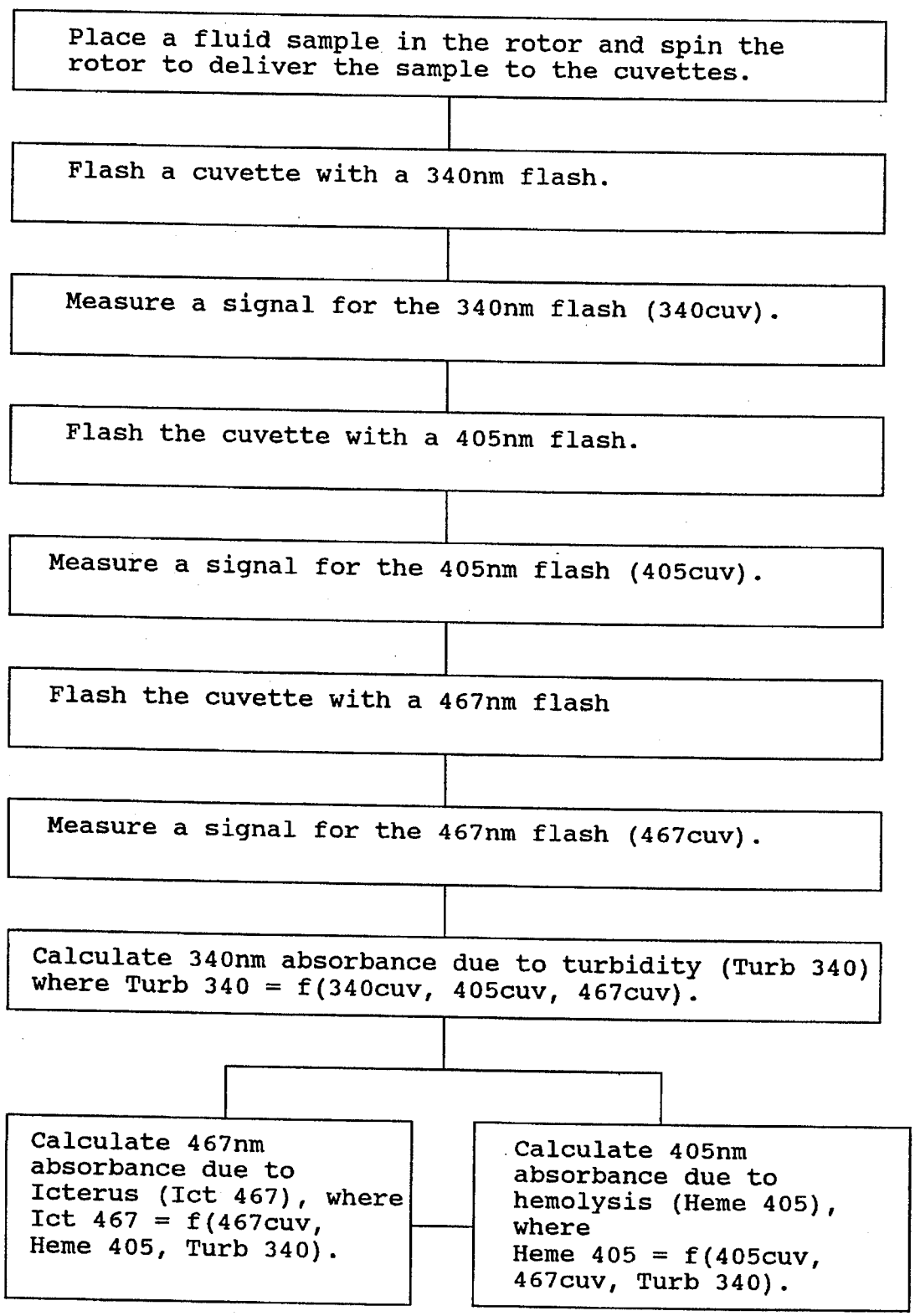
FIG. 11 is a flow chart illustrating a method for determining whether a blood sample in a cuvette of an analytical rotor is hemolyzed, lipemic, or icteric.

FIG. 11 illustrates a method used to determine if a blood sample is hemolyzed, lipemic, or icteric. This test is particularly useful for whole-blood analyzers where the user is not given a chance to visualize the serum or plasma and judge its hemolysis, lipemia, or icteric content. The method of the present invention determines these levels by placing the blood in the rotor and spinning the rotor to deliver the plasma to the cuvettes. A cuvette having a sample blank reagent is then flashed with a series of light flashes having three different wavelengths. Preferably, the wavelengths will be about 340 nm, 405 nm, and 467 nm. A corresponding signal is measured for each of the three flashes. These three wavelengths are then compared in an iterative manner to determine whether the sample is hemolyzed, lipemic, or icteric. The calculations used in this comparison are referred to as sample index calculations. If one of these conditions is satisfied, an error condition is indicated.

The sample blank reagent is a reagent, which when dried and placed in the cuvette, will clear plasma or serum samples quickly to an endpoint which can be read at the wavelengths needed to determine the turbid, hemolytic and icteric nature of the sample. This improves the precision and accuracy of the sample index calculations. Without this reagent, there is often an appreciable rate of change in these absorbances, making robust calculations more difficult and prone to noise. The sample blank reagent also helps prevent precipitation in samples, which may also make the calculations less useful.

The contents of an exemplary bead that is particularly useful for clearing samples in order to determine the sample indices is shown in Table 1. Typically, when preparing the dried reagent, this solution is used at one-sixth of the cuvette volume.

TABLE 1

| Material | Quantity (#/L) |
| --- | --- |
| Tris Base | 14.9 g |
| Trethano amine-HCl | 44.6 g |
| NaCl | 45.0 g |
| Polyethylene glycol (PEG) 8000 | 50.0 g |
| PEG 3400 | 46.0 g |
| Triton X-100 | 8.0 g |
| Heparin, lithium | 80,000 units |
| Sodium azide | 0.5 g |
| HCl | as needed |
| NaOH | as needed |
| Adjust to pH 7.4–7.6 | |
| Q.S. to 1,000 ml | |
| Filter | |

An exemplary method for determining whether the sample is hemolyzed, lipemic, or icteric, is as follows. After the signals have been measured for the three different flashes, the absorbance values are stored as $A_{340}$, $A_{405}$, and $A_{467}$. These represent the absorption values at 340 nm, 405 nm, and 467 nm, respectively. The 340 nm absorbance is dominated by turbidity, but it is also affected by hemolysis and icterus. The 340 nm, 405 nm, and 467 nm absorbances are dominated by turbidity, hemolysis, and icterus, respectively. They are also affected by other interferences as well. These effects can be accounted for using the following sample index equations:

$$A_{340\text{-}turbidity} = A_{340} - aA_{467\text{-}icterus} - bA_{405\text{-}hemolysis}$$

$$A_{405\text{-}hemolysis} = A_{405} - cA_{467\text{-}icterus} - dA_{340\text{-}turbidity}$$

$$A_{467\text{-}icterus} = A_{467} - eA_{405\text{-}hemolysis} - fA_{340\text{-}turbidity}$$

The constants "a" through "f" are determined empirically.

A further source of error can be in the handling of rotors after they leave the manufacturer's warehouse. Typically, the rotors are packaged in impermeable foil pouches with a desiccant pouch inside. The rotors are shipped in cold packs to users who store them in cold storage, such as a refrigerator. Before use, the rotors are typically brought to room temperature for at least 20 minutes and generally no longer than 120 hours. Some of the chemistries are adversely affected by exposure to heat, humidity, light, and other environmental conditions.

Figure 12:
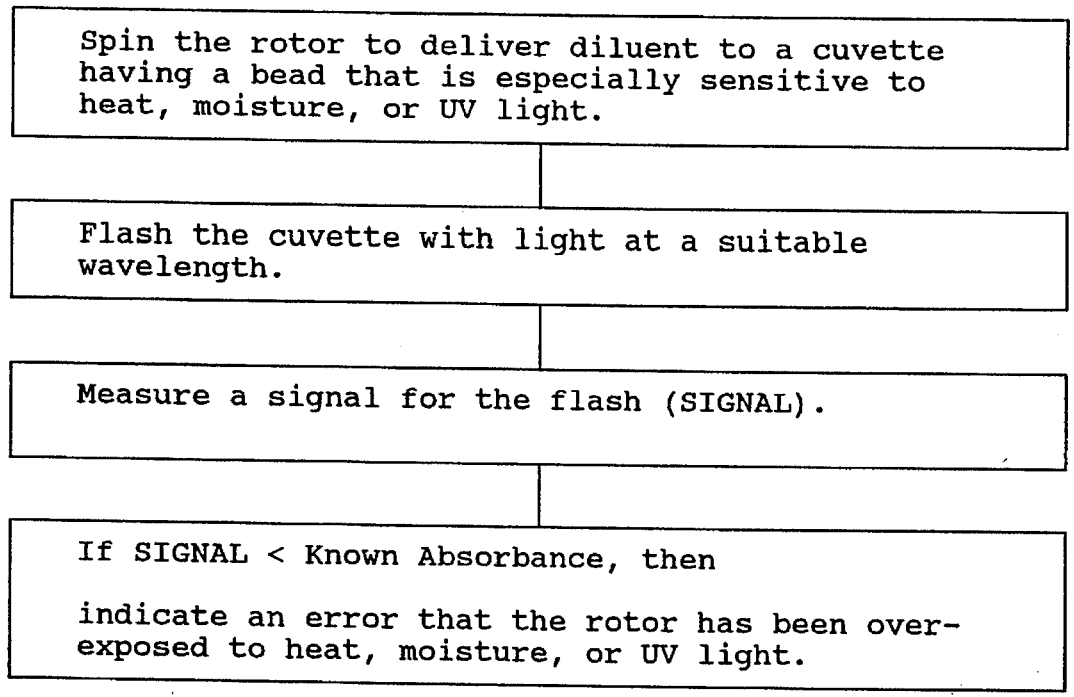
FIG. 12 is a flow chart illustrating a method for determining the degradation of a reagent within a cuvette of an analytical rotor.

To determine whether any of the reagents may have been affected by excessive exposure to such conditions, the method as illustrated in FIG. 12 is used to generate an error condition if the rotor has been overexposed to heat, moisture, or to UV or other light. The check is performed by providing at least one test reagent in at least one cuvette which is more sensitive to heat, light, moisture, or other environmental conditions than all other analytical reagents in other cuvettes of the rotor. When the rotor is spun in the analyzer, only diluent is delivered to the cuvette having the test reagent(s). Light is then directed through the test cuvette and a signal is measured. If the signal differs by a predetermined amount from an expected value, the error condition is indicated.

In a preferred aspect, the rotor will contain two cuvettes, one with reagent bead(s) sensitive to heat and humidity, the other to light and heat. An exemplary reagent system that is more sensitive to heat and humidity includes a uric acid analyte bead A and a uric acid detector bead B. The compositions of the A and B beads are shown in Tables 2 and 3, respectively. The reagent bead system has been found to be particularly sensitive to heat and humidity. Thus, so long as this system remains active and produces a correct reading of the known amount of uric acid, it can be assumed that the less sensitive reagents also remain active and non-degraded by heat and humidity. When the uric acid reagent is in the test cuvette, light having a wavelength of about 500 nm will preferably be flashed through the cuvette to produce the signal.

TABLE 2

Uric Acid Analyte Bead A

| Material | Quantity Per Liter |
|---|---|
| Deionized water | 1.00 L |
| HEPES | 40.00 g |
| Triton X100-PC | 3.00 g |
| Polyethylene glycol, 8000 | 15.00 g |
| D-Mannitol | 100.00 g |
| Dextran, low fraction | 20.00 g |
| Potassium ferrocyanide | 0.16 g |
| DHBSA | 10.00 g |
| Uric acid | 11.5 mg |
| Potassium hydroxide solution, 5N | As needed |
| Hydrochloric acid solution, 2N | As needed |

TABLE 3

Uric Acid Detector Bead B

| Material | Quantity Per Liter |
|---|---|
| Deionized water | 1.00 L |
| HEPES | 40.00 g |
| Triton X100-PC | 3.00 g |
| Polyethylene glycol, 8000 | 15.00 g |
| D-Mannitol | 100.00 g |
| Dextran, low fraction | 20.00 g |
| Bovuminar reagent pure powder | 9.00 g |
| 4-AAP | 1.56 g |
| Peroxidase | 8,000 U |
| Uricase | 2,000 U |
| Potassium hydroxide solution, 5N | As needed |
| Hydrochloric acid solution, 2N | As needed |

Typically, when preparing the dried reagent from the concentrated solutions in Tables 2 and 3, the solutions are used at one-fourth of the cuvette volume so that the final reagent concentration in the cuvette is at the desired level.

The contents of an exemplary reagent that is particularly sensitive to light is shown in Table 4. The reagent of Table 4 has been found to be particularly sensitive to light. Thus, so long as the reagent remains active and produces a correct reading of the known amount of reagent, it can be assumed that the less sensitive reagents also remain active and non-degraded by light. Preferably, light having a wavelength of about 467 nm is flashed through the test cuvette containing the reagent of Table 4.

TABLE 4

| Material | Quantity (g/l) |
|---|---|
| Tris Base | 14.9 |
| Triethanolamine | 44.6 |
| Sodium chloride | 45 |
| PEG 8000 | 50 |
| PEG 3400 | 46 |
| Triton X-100 | 8 |
| Sodium azide | 0.5 |
| Bilirubin conjugate | 0.45 |
| HCL | As needed |
| Adjust to pH 7.4–7.6 | |
| Q.S to 50 ml | |
| Filter | |

Typically, when preparing the dried reagent from the concentrated solution in Table 4, the solution is used at one-sixth of the cuvette volume.

Figure 13:
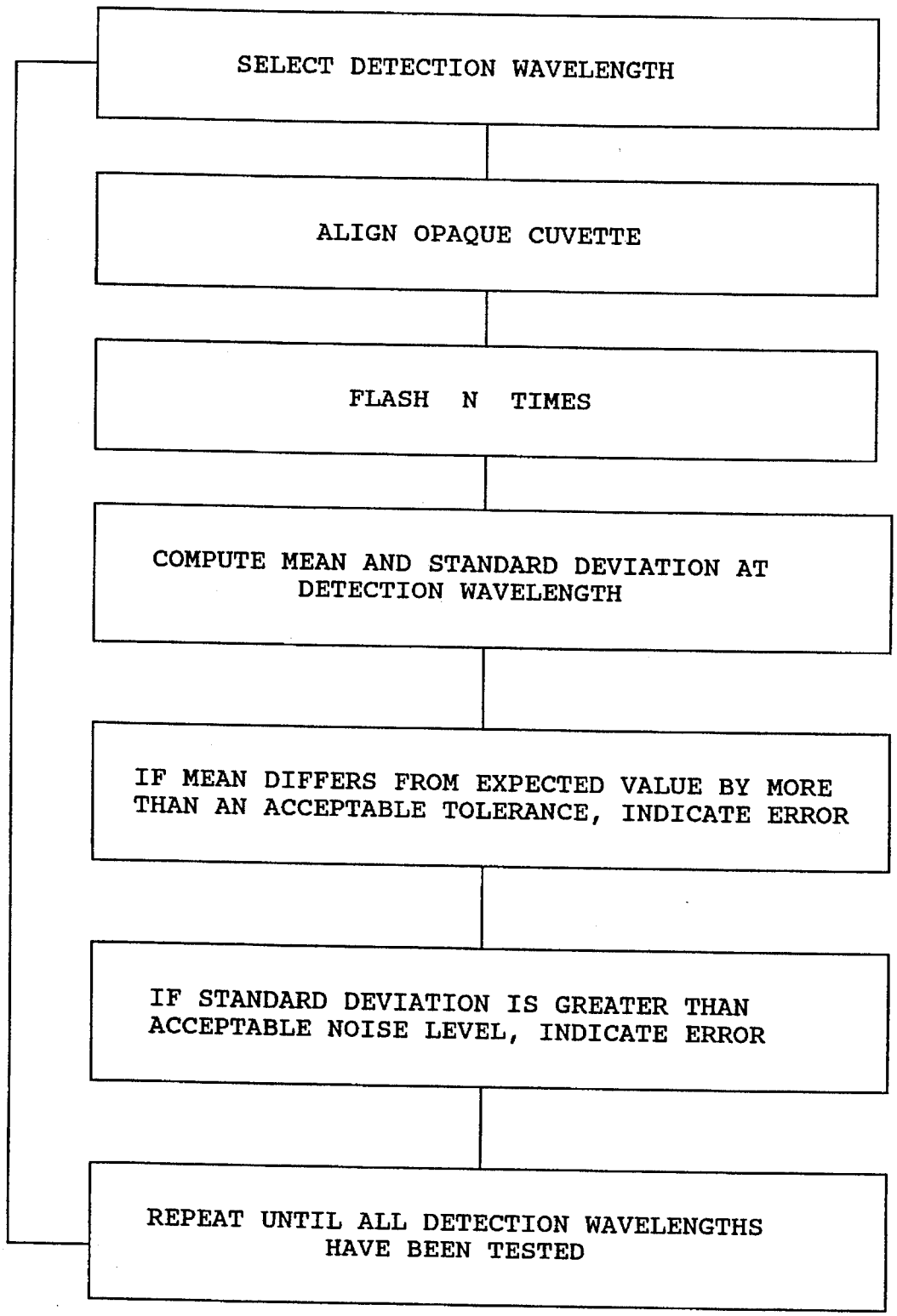
FIG. 13 is a flow chart illustrating a method for determining proper light source and light detector function under full light conditions.
Figure 14:
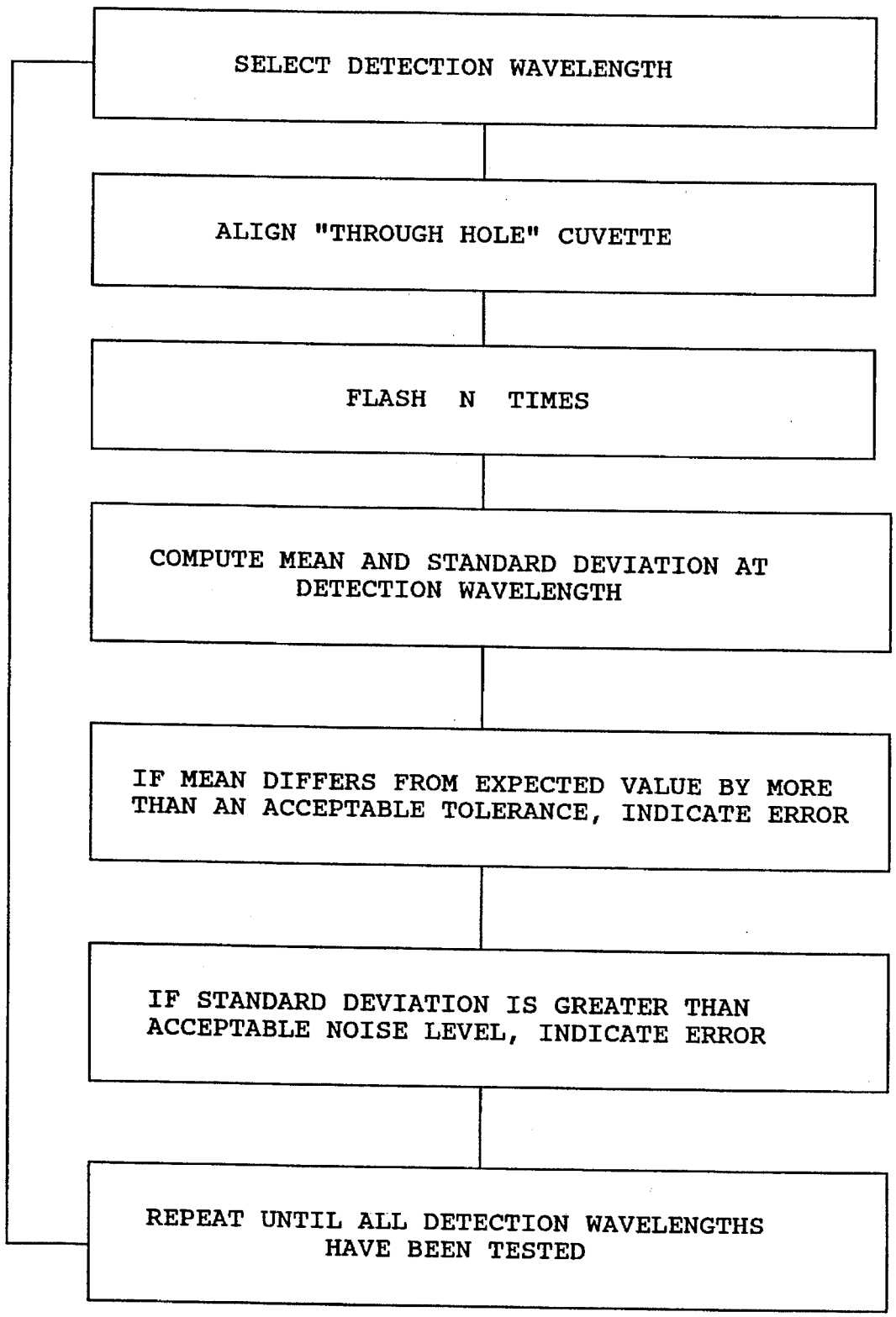
FIG. 14 is a flow chart illustrating a method for determining proper light source and light detector function under blocked light conditions.

Referring to FIGS. 13 and 14, proper functioning of the light source, typically an arc lamp, and associated light detection circuitry will be checked every time the system is run. First, as set forth in FIG. 13, system response under blocked light conditions is checked at each detection wavelength. As the rotor is spun, the light is flashed and the output of a first wavelength detector is measured over N (usually 50) flashes. The mean value and standard deviation at the first wavelength is then calculated. A mean value which falls outside the expected range indicates that the particular detection is malfunctioning, and an appropriate error condition is signalled. A standard deviation outside of an acceptable range indicates that excessive noise is present, and an appropriate error condition is signalled. These test steps will be repeated for each detection wavelength. Once all wavelengths are confirmed to be acceptable, the testing can continue. Alternatively, a range can be used in the analysis instead of the standard deviation.

Referring to FIG. 14, the system response under full light conditions is also checked at each detection wavelength prior to system operation. The test protocol is almost identical to the blocked light test of FIG. 13, except that detection occurs when the open (through hole) cuvette is aligned between the light source and detector. Again mean values and standard deviations (or a range) will be calculated at each wavelength. A mean value which falls outside the expected range will indicate either light source error, light detection error, or both. A standard deviation outside an acceptable range is a likely sign of excessive electronic or optical noise produced by the arc lamp or indicative of other instrument problems. The test is repeated at each wavelength, and an error condition is indicated whenever a measured value falls outside of the expected range.

Referring now to FIG. 15, motor operation and ability to properly read certain "cuvette marks" on the rotor will be checked prior to each system run. The cuvette marks are provided as surfaces 50 (FIG. 16) which reflect light provided by an LED disposed below the rotor and which are detectable by a light detector disposed at the edge of the rotor. Detection of each cuvette mark signals the analyzer that another cuvette has passed and allows the system to keep track of which cuvette is being analyzed. An index mark 52, which is approximately twice as wide as the other cuvette marks 50 allows initial orientation of the rotor within the system.

The rotor is spun at a predetermined steady speed. The index mark 52 is identified based on its width (where width equals time depending on the speed of rotation). After the index mark 52 is located, the threshold detection level from the light detector is adjusted until the width of detection for the index mark is within an acceptable range. The width of each individual cuvette mark 50 is then measured and an error condition is indicated if the width falls outside of the expected range. Such an error can occur if the cuvette mark has been improperly manufactured and does not have the specified width or detectability. The distance between marks is also checked, and an error is indicated if an mark appears sooner than it should (possibly as the result of reflection from a manufacturing defect in the rotor). As an additional check, the total number of cuvette marks 50 between successive appearances of the index mark 52 is counted and checked against the expected number, i.e. 29. Finally, the motor speed is calculated based on the rate of passage of the cuvette marks. If any of the measured or calculated values falls outside of the expected range, an appropriate error condition is signalled.

The invention has been described in some detail for the purposes of clarity and illustration. Modifications to the particular embodiments described will occur to those skilled in the art. Therefore, the scope of the invention should be determined with reference to the appended claims, along with the full scope of equivalence to which those claims are entitled.

What is claimed is:

1. A method for confirming the presence of a reagent in sample receptacles of a receptacle holder before a fluid sample is applied to the sample receptacles, the receptacle holder being used with a fluid analyzer having alight source and a light detector disposed to detect light directed through the sample receptacles, the method comprising the steps of:

directing light through each sample receptacle, wherein at least some of the sample receptacles contain a reagent before the fluid sample is applied;

measuring a signal from the light detector for each sample receptacle while the light is directed through each sample receptacle;

directing light between the light source and the light detector through an open aperture in the sample receptacle or in the absence of the sample receptacle and measuring a reference signal;

comparing the measured signals for each sample receptacle with the reference signal to produce a comparison value for each sample receptacle;

indicating an error condition if the comparison value for any sample receptacle that should contain the reagent differs by at least a predetermine amount from a first value expected when the reagent is present; and introducing an amount of the liquid sample to at least one of the sample receptacles if no error condition is indicated.

2. The method of claim 1, wherein the comparison value for each sample receptacle is obtained by dividing the measured signals for each sample receptacle by the measured signal for the open aperture, and wherein the error is indicated if the comparison value is greater than the first expected value.

3. The method of claim 1, further comprising indicating an error condition if the comparison value for any sample receptacle that should not contain the reagent differs by at least a predetermined amount from a second expected value when the reagent is absent.

4. The method of claim 3, wherein the comparison value for each sample receptacle is obtained by dividing the measured signals for each sample receptacle by the measured signal for the open aperture, and wherein the error is indicated if the comparison value is less than the second expected value.

5. The method of claim 1, wherein the receptacle holder comprises an analytic rotor, and wherein the sample receptacles comprise cuvettes.

6. A method for determining whether a fluid sample has been properly distributed to sample receptacles located about the periphery of an analytical rotor, the analytical rotor being used with a fluid analyzer having a light source and a light detector disposed to detect light directed through the sample receptacles, the method comprising the steps of:

applying an amount of the fluid sample to the rotor;

spinning the rotor to distribute aliquots of the applied fluid sample in selected sample receptacles;

directing light through each sample receptacle;

measuring a signal from the light detector for each sample receptacle while the light is directed through each sample receptacle;

directing light between the light source and the light detector through an open aperture in the analytical rotor or in the absence of the analytical rotor and measuring a reference signal;

comparing the measured signals for each sample receptacle with the reference signal to produce a comparison value for each sample receptacle; and indicating an error condition when the comparison value for any sample receptacle differs by at least a predetermined amount from a value expected when a proper amount of the fluid sample is present in the sample receptacle, wherein the error condition indicates that a proper distribution of the fluid sample is not present in each sample receptacle.

7. The method of claim 6, further comprising combining the fluid sample with a diluent prior to delivering aliquots of the sample to the selected sample receptacles.

8. The method of claim 6, wherein the comparison value for each sample receptacle is obtained by dividing the measured signals for each sample receptacle by the reference signal, and wherein the error is indicated if the comparison value is less than the expected value, wherein the light has a wavelength of about 850 nm and wherein the expected value is about 0.3.

9. The method of claim 6, wherein the sample receptacles comprise cuvettes.

10. A method for determining whether a fluid sample has been properly distributed to sample receptacles located about a periphery of an analytic rotor, the receptacles being disposed such that the fluid sample is sequentially delivered to the sample receptacles upon rotation of the rotor, the analytical rotor being used with a fluid analyzer having a light source and a light detector disposed to detect light directed through the sample receptacle, the method comprising the steps of:

applying an amount of the fluid sample to the rotor;

spinning the rotor;

directing light through a first one of the sample receptacles which is disposed to first receive the fluid sample, the light having a wavelength which is selectively absorbed by the fluid sample but not by the diluent;

measuring a signal from the light detector for the first sample receptacle while the light is directed through the first sample receptacle;

comparing the signal measured from the first sample receptacle with a value expected when sample is present; and indicating an error condition when the signal measured from the first sample receptacle differs by at least a predetermined amount from the expected value.

11. The method of claim 10, wherein light is directed through the first sample receptacle at a wavelength of about 340 nm.

12. The method of claim 10, wherein the sample receptacles comprise cuvettes.

13. A method for determining whether a fluid sample has been properly mixed with a diluent prior to distribution to a plurality of sample receptacles of a receptacle holder, with at least some of the sample receptacles containing a reagent and with at least some of the sample receptacles not containing a reagent, the receptacle holder being used with a fluid analyzer having a light source and a light detector disposed to detect light directed individually through each sample receptacle, the method comprising the steps of:

delivering a mixture of the diluent and the fluid sample to the sample receptacles so that both the sample receptacles containing reagent and not containing reagent receive the mixture;

directing light through a multiplicity of the sample receptacles not having reagent, the light having a wavelength which is differentially absorbed by mixtures having different ratios of the fluid sample and the diluent;

measuring a signal from the light detector for each of the multiplicity of the sample receptacles not having reagent while the light is directed through the sample receptacles;

comparing the signals measured from at least some of the multiplicity of the sample receptacles not having reagent with each other; and indicating an error condition if the range of the compared signals exceed an expected range.

14. The method of claim 13, wherein the measured signal are compared by dividing the measured signal for each of the multiplicity of sample receptacles with each other.

15. The method of claim 14, wherein light is directed through the sample receptacle at a wavelength of about 340 nm.

16. The method of claim 13, wherein the receptacle holder comprises an analytic rotor, and the sample receptacles comprises cuvettes, and wherein the fluid sample is delivered to the cuvettes by spinning the rotor.

17. A method for determining whether a diluent distributed to sample receptacles of a receptacle holder is contaminated, the receptacle holder being used with a fluid analyzer having a light source and a light detector disposed to detect light directed through the sample receptacles, the method comprising the steps of:

distributing diluent from a diluent source to a sample receptacle without combination with sample and without combination with reagent;

directing light through the sample receptacle which received the diluent without combination with sample and reagent, the light having a wavelength which is differentially absorbed by diluent having differing amounts of contamination;

measuring a signal from the light detector for the sample receptacle while the light is directed through the sample receptacle;

comparing the signal measured from the sample receptacle with an expected value; and indicating an error condition if the measured signal differs by at least a predetermined amount from the expected value.

18. The method of claim 17, wherein the error is indicated if the value of the measured signal is greater than the expected value.

19. The method of claim 18, wherein light is directed through the sample receptacle at a wavelength of about 340 nm.

20. The method of claim 17, wherein the receptacle holder comprises an analytic rotor, and wherein the sample receptacles comprise cuvettes.

21. A method for determining systematic errors when measuring different reaction chemistries in sample receptacles of a receptacle holder, the receptacle holder being used with a fluid analyzer having a light source and a light detector disposed to detect light directed through the sample receptacle, the method comprising the steps of:

delivering aliquots of the fluid sample to each sample receptacle;

directing light through each sample receptacle;

measuring a signal from the light detector for each sample receptacle while the light is directed through each sample receptacle;

comparing each signal measured from each sample receptacle with an associated expected value, the associated expected value being associated with the reaction chemistry in each sample receptacle;

computing a summation of the total number of sample receptacles whose measured signals differ by at least a predetermined amount from each associated expected value; and indicating an error condition if the summation is greater than an acceptable value.

22. The method of claim 21, wherein the receptacle holder comprises an analytic rotor and the sample receptacles comprise cuvettes, and wherein the aliquots of the sample are delivered by spinning the rotor.

23. A method for determining whether a sample in a sample receptacle of a receptacle holder is hemolyzed, lipemic, or icteric, the receptacle holder being used with a fluid analyzer having a light source and a light detector disposed to detect light directed through the sample receptacle, the method comprising the steps of:

placing the sample in the sample receptacle;

directing light having a first wavelength through the sample receptacle;

measuring a signal from the light detector for the sample receptacle while the light having the first wavelength is directed through the sample receptacle;

directing light having a second wavelength through the sample receptacle;

measuring a signal from the light detector for the sample receptacle while the light having the second wavelength is directed through the sample receptacle;

directing light having a third wavelength through the sample receptacle;

measuring a signal from the light detector for the sample receptacle while the light having the third wavelength is directed through the sample receptacle;

comparing the three signals measured from the sample receptacle for each of the three wavelengths in an iterative fashion to determine whether the sample is hemolyzed, lipemic, or icteric; and indicating an error condition if the sample is hemolyzed, lipemic, or icteric.

24. The method of claim 23, wherein the first wavelength is about 340 nm, the second wavelength is about 405 nm, and the third wavelength is about 467 nm.

25. The method of claim 24, further comprising determining whether the sample is lipemic by subtracting a fraction of the value of the measurement at the second wavelength and a fraction of the value of the measurement at the third wavelength from the value of the measurement at the first wavelength to obtain a turbidity absorbance value.

26. The method of claim 25, further comprising determining whether the sample is hemolyzed by subtracting a fraction of the value of the measurement at the third wavelength and a fraction of the turbidity absorbance value from the value of the measurement at the second wavelength to obtain a hemolysis absorbance value.

27. The method of claim 26, further comprising determining whether the sample is icteric by subtracting a fraction of the hemolysis absorbance value and a fraction of the turbidity absorbance value from the value of the measurement at the third wavelength to obtain a hemolysis absorbance value.

28. The method of claim 23, wherein the sample receptacle contains a sample blank reagent.

29. The method of claim 23, wherein the receptacle holder comprises an analytic rotor and the sample receptacles comprise cuvettes.

30. The method for determining malfunction in an analyzer having a light source and a light detector, said method comprising:

measuring light from the light source with the light detector with substantially no interfering substances between the light source and light detector;

comparing the measured light intensity with an expected value; and indicating an error condition signaling malfunction of the analyzer if the measured value differs from the expected value by more than a predetermined amount.

31. A method as in claim 30, wherein the light intensity is measured and compared at each of a plurality of wavelengths, wherein the error condition is indicated if the measured value is outside of the expected range at any one wavelength.

32. A method as in claim 31, wherein light is measured at each wavelength a plurality of times.

33. A method for determining malfunction in an analyzer having a light source and a light detector, said method comprising:

measuring light from the light source with the light detector with the light path between the light source and light detector being substantially blocked, wherein light is measured at each wavelength a plurality of times;

comparing the measured light intensity with an expected value; and indicating an error condition signaling malfunction of the analyzer if the measured value differs from the expected value by more than a predetermined amount;

wherein the light intensity is measured and compared at each of a plurality of wavelengths, wherein the error condition is indicated if the measured value is outside of the expected range at any one wavelength, wherein a mean value is determined for the plurality of measurements at each wavelength and the mean value is compared with the expected value; and indicating an error condition signaling malfunction of the analyzer if the mean value for at least one wavelength differs from the expected value by more than a predetermined amount.

34. The method for determining malfunction in an analyzer having a light source and a light detector, said method comprising:

measuring light from the light source with the light detector with substantially no interfering substances between the light source and light detector, wherein light is measured at each wavelength a plurality of times;

comparing the measured light intensity with an expected value; and indicating an error condition signaling malfunction of the analyzer if the measured value differs from the expected value by more than a predetermined amount;

wherein the light intensity is measured and compared at each of a plurality of wavelengths, wherein the error condition is indicated if the measured value is outside of the expected range at any one wavelength, wherein a mean value is determined for the plurality of measurements at each wavelength and the mean value is compared with the expected value; and indicating an error condition signaling malfunction of the analyzer if the mean value for at least one wavelength differs from the expected value by more than a predetermined amount.

35. The method for determining malfunction in an analyzer having a light source and a light detector, said method comprising:

measuring light from the light source with the light detector with substantially no interfering substances between the light source and light detector, wherein light is measured at each wavelength a plurality of times;

comparing the measured light intensity with an expected value; and indicating an error condition signaling malfunction of the analyzer if the measured value differs from the expected value by more than a predetermined amount;

wherein the light intensity is measured and compared at each of a plurality of wavelengths, wherein the error condition is indicated if the measured value is outside of the expected range at any one wavelength, wherein a standard deviation or a range is determined for the plurality of measurements at each wavelength and an error condition is indicated if the standard deviation or range for at least one wavelength exceeds an acceptable value.

36. A method for determining malfunction in an analyzer having a light source and a light detector, said method comprising:

measuring light from the light source with the light detector with the light path between the light source and light detector being substantially blocked;

comparing the measured light intensity with an expected value;

indicating an error condition signaling malfunction of the analyzer if the measured value differs from the expected value by more than a predetermined amount;

wherein the light intensity is measured and compared at each of a plurality of wavelengths, wherein light is measured at each wavelength a plurality of times, wherein the error condition is indicated if the measured value is outside of the expected range at any one wavelength; wherein a standard deviation or a range is determined for the plurality of measurements at each wavelength and an error condition is indicated signalling analyzer malfunction if the standard deviation or range for at least one wavelength exceeds an acceptable value.

* * * * *